US009395302B2

(12) United States Patent
Holmes et al.

(10) Patent No.: US 9,395,302 B2
(45) Date of Patent: Jul. 19, 2016

(54) IMAGE ANALYSIS AND MEASUREMENT OF BIOLOGICAL SAMPLES

(71) Applicant: Theranos, Inc., Palo Alto, CA (US)

(72) Inventors: Elizabeth A. Holmes, Palo Alto, CA (US); Chinmay Pangarkar, Palo Alto, CA (US); Timothy Smith, Palo Alto, CA (US); Karan Mohan, Palo Alto, CA (US); Samartha Anekal, Palo Alto, CA (US); Daniel L. Young, Palo Alto, CA (US); James R. Wasson, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 63 days.

(21) Appl. No.: 13/951,449

(22) Filed: Jul. 25, 2013

(65) Prior Publication Data

US 2014/0030737 A1  Jan. 30, 2014

Related U.S. Application Data

(60) Provisional application No. 61/675,811, filed on Jul. 25, 2012, provisional application No. 61/676,178, filed on Jul. 26, 2012, provisional application No. 61/766,116, filed on Feb. 18, 2013, provisional application No. 61/802,194, filed on Mar. 15, 2013.

(51) Int. Cl.
| | |
|---|---|
| *G01N 21/03* | (2006.01) |
| *G01N 21/64* | (2006.01) |
| *B01L 3/00* | (2006.01) |
| *G01N 33/569* | (2006.01) |
| *G02B 7/09* | (2006.01) |
| *G01N 21/05* | (2006.01) |
| *G02B 21/08* | (2006.01) |

(Continued)

(52) U.S. Cl.
CPC ...... *G01N 21/6486* (2013.01); *B01L 3/502715* (2013.01); *G01N 21/0303* (2013.01); *G01N 21/05* (2013.01); *G01N 21/17* (2013.01); *G01N 21/645* (2013.01); *G01N 21/6458* (2013.01); *G01N 33/487* (2013.01); *G01N 33/56972* (2013.01); *G02B 7/09* (2013.01); *G02B 21/0076* (2013.01); *G02B 21/088* (2013.01); *G02B 21/125* (2013.01); *G02B 21/244* (2013.01); *G01N 2201/061* (2013.01); *G01N 2201/12* (2013.01)

(58) Field of Classification Search
CPC ... G01N 21/05; G01N 21/0303; G01N 30/74; G01N 2021/0346; G01N 21/645
See application file for complete search history.

(56) References Cited

U.S. PATENT DOCUMENTS

| | | |
|---|---|---|
| 3,849,654 A | 11/1974 | Malvin |
| 3,854,044 A | 12/1974 | Stay et al. |

(Continued)

FOREIGN PATENT DOCUMENTS

| | | |
|---|---|---|
| CN | 201156031 | 11/2008 |
| EP | 0781987 A2 | 7/1997 |

(Continued)

OTHER PUBLICATIONS

U.S. Appl. No. 14/600,630, filed Jan. 20, 2015.

(Continued)

*Primary Examiner* — Erik B Crawford

(57) ABSTRACT

Methods, devices, systems, and apparatuses are provided for the image analysis of measurement of biological samples.

15 Claims, 11 Drawing Sheets

(51) Int. Cl.
*G01N 21/17* (2006.01)
*G02B 21/00* (2006.01)
*G02B 21/12* (2006.01)
*G02B 21/24* (2006.01)
*G01N 33/487* (2006.01)

(56) References Cited

U.S. PATENT DOCUMENTS

| | | | |
|---|---|---|---|
| 5,292,484 | A | 3/1994 | Kelln et al. |
| 5,414,508 | A | 5/1995 | Takahashi et al. |
| 6,088,097 | A | 7/2000 | Uhl |
| 6,396,580 | B1 | 5/2002 | Tewes |
| 6,599,475 | B1 * | 7/2003 | Berndt et al. .......... 422/401 |
| 8,313,713 | B2 * | 11/2012 | Jacobs et al. .......... 422/554 |
| 2001/0028497 | A1 | 10/2001 | Uhl |
| 2003/0104494 | A1 | 6/2003 | Ravkin et al. |
| 2003/0202905 | A1 | 10/2003 | Devlin et al. |
| 2003/0205681 | A1 | 11/2003 | Modlin |
| 2003/0236458 | A1 | 12/2003 | Hochman |
| 2004/0126005 | A1 | 7/2004 | Duvdevani et al. |
| 2005/0030541 | A1 | 2/2005 | Erlbacher et al. |
| 2005/0237605 | A1 | 10/2005 | Vodyanoy et al. |
| 2006/0043301 | A1 | 3/2006 | Mantele et al. |
| 2006/0215400 | A1 * | 9/2006 | Lewis et al. .......... 362/233 |
| 2007/0035818 | A1 | 2/2007 | Bahatt et al. |
| 2007/0146717 | A1 * | 6/2007 | Prins ............ B01L 3/502715 356/445 |
| 2009/0190822 | A1 | 7/2009 | Ortyn et al. |
| 2010/0128256 | A1 | 5/2010 | Thomson |
| 2011/0064628 | A1 | 3/2011 | Thomas et al. |
| 2013/0088221 | A1 * | 4/2013 | Van Zon ............ B82Y 25/00 324/228 |
| 2014/0038206 | A1 | 2/2014 | Holmes et al. |
| 2014/0273188 | A1 | 9/2014 | Mohan et al. |

FOREIGN PATENT DOCUMENTS

| | | |
|---|---|---|
| JP | 2007127449 A | 5/2007 |
| WO | 2002093141 A1 | 11/2002 |
| WO | 2012178069 A | 12/2012 |
| WO | 2014018805 A2 | 1/2014 |
| WO | 2014127372 A2 | 8/2014 |

OTHER PUBLICATIONS

The International Search Report and the Written Opinion dated Mar. 24, 2014 for Application No. PCT/US2013/052141.

U.S. Appl. No. 14/167,964, filed Jan. 29, 2014. Inventors: Mohan, et al.

International Search Report and Written Opinion dated Sep. 11, 2014 for Application No. PCT/US2014/016962.

U.S. Appl. No. 14/508,137, filed Oct. 7, 2014.

Office Action dated Jan. 15, 2016 for U.S. Appl. No. 14/508,137.

Office Action dated Jan. 4, 2016 for U.S. Appl. No. 14/161,639.

Office Action dated Jun. 12, 2015 for U.S. Appl. No. 14/161,639.

Office Action dated Jun. 5, 2015 for U.S. Appl. No. 14/508,137.

Office Action dated Jul. 8, 2015 for U.S. Appl. No. 13/951,063.

Office Action dated Sep. 21, 2015 for U.S. Appl. No. 14/508,137.

Dhawan et al. Multispectral Optical Imaging of Skin-Lesions for Detection of Malignant Melanomas. Proceeding of the 31st Annual International Conference of the IEEE Engineering in Medicine and Biology Society: Engineering the Future of Biomedicine, EMBC 2009, IEEE, Sep. 3, 2009, pp. 5352-5355.

Lee et al. Integrated optical molecular imaging system for four-dimensional real-time detection in living single cells, Biosensors and Bioelectronics, Elsevier BV, NL, vol. 31 No. 1, Oct. 27, 2011, pp. 393-398.

Thompson, Fluorescence Correlation Spectroscopy, Topics in Fluorescence Spectroscopy, Jan. 1, 2002, Kluwer Academic Publishers, Boston.

Advisory Action dated Apr. 28, 2016 for U.S. Appl. No. 13/951,063.

Notice of Allowance dated Apr. 14, 2016 for U.S. Appl. No. 14/161,639.

Office Action dated Feb. 24, 2016 for U.S. Appl. No. 13/951,063.

Office Action dated May 12, 2016 for U.S. Appl. No. 14/508,137.

\* cited by examiner

IMAGE ANALYSIS AND MEASUREMENT OF BIOLOGICAL SAMPLES

BACKGROUND

Analysis of biological samples from a subject may be important for health-related diagnosing, monitoring and/or treating of the subject. A variety of methods are known for the analysis of biological samples. However, in order to provide better diagnosing, monitoring, and/or treating of subjects, improvements in the analysis of biological samples are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Methods, devices, systems, and apparatuses are described herein for image analysis and/or measurement of biological samples.

In one embodiment, a method for the measurement of a component of interest in cells of a cellular population in a sample is provided, including: a) obtaining a quantitative measurement of a marker present in cells of the cellular population in the sample; b) based on the measurement of part a), determining, with the aid of a computer, an approximate amount of cells in the cellular population present in the sample; c) based on the results of part b), selecting an amount of reagent to add to the sample, wherein the reagent binds specifically to the component of interest in cells of the cellular population and is configured to be readily detectable; d) based on the results of part c), adding the selected amount of the reagent to the sample; e) assaying cells in the sample for reagent bound to the compound of interest; and f) based on the amount of reagent bound to the compound of interest, determining the amount of the component of interest in cells of the cellular population of the sample. In an embodiment of the method, the reagent of part c) is an antibody.

In another embodiment, a method for focusing a microscope is provided, including: a) mixing a sample containing an object for microscopic analysis with a reference particle having a known size, to generate a mixture containing the sample and reference particle; b) positioning the mixture of step a) into a light path of a microscope; c) exposing the mixture of step a) to a light beam configured to visualize the reference particle; and d) focusing the microscope based on the position of the reference particle within the mixture.

In yet another embodiment, provided herein is a method for identifying a cell in a sample containing a plurality of cells, including: a) assaying a cell of the plurality of cells for at least one of: (i) the presence of a cell surface antigen; (ii) the amount of a cell surface antigen; or (iii) cell size; b) assay the cell of a) for at least one of: (i) nuclear size; or (ii) nuclear shape; and c) assaying the cell of a) and b) for quantitative cell light scatter, wherein the combination of information from steps a), b) and c) is used to identify the cell in the sample containing a plurality of cells.

It should be understood that embodiments in this disclosure may be adapted to have one or more of the features described in this disclosure.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1A:
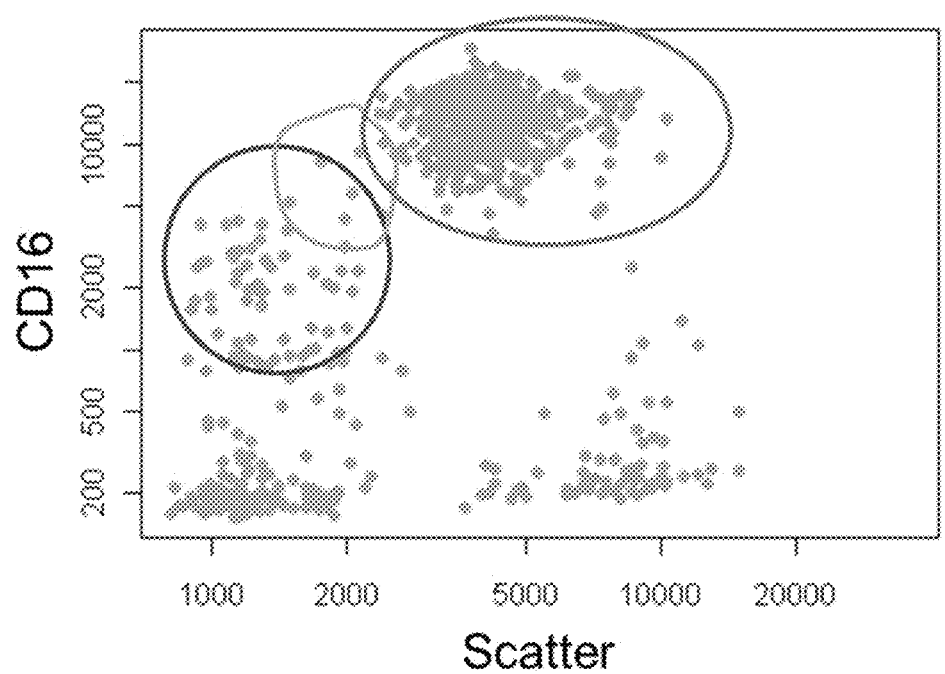
FIG. 1 shows: (A) a plot of side scatter intensity x-axis) vs. fluorescence intensity of a mixture cells including natural killer cells and neutrophils labeled with a fluorescent binder that recognizes CD16; (B) a bar graph showing the ratio of nuclear area to total cell area of natural killer cells ("NK") and neutrophils ("Neu"); (C) natural killer cells stained with anti-CD16 antibody (left column) and a nuclear stain (right column); (D) neutrophils stained with anti-CD16 antibody (left column) and a nuclear stain (right column).

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection well, this means that the sample collection well may or may not be present, and, thus, the description includes both structures wherein a device possesses the sample collection well and structures wherein sample collection well is not present.

The term "cells," as used in the context of biological samples, encompasses samples that are generally of similar sizes to individual cells, including but not limited to vesicles (such as liposomes), cells, virions, and substances bound to small particles such as beads, nanoparticles, or microspheres.

Quantitative Microscopy

In some embodiments, methods, systems, and devices are provided herein for quantitative microscopy. Quantitative microscopy may involve one or more of quantitative fluorescence microscopy, quantitative dark field microscopy, quantitative bright field microscopy, and quantitative phase contrast microscopy methods to measure one or more cellular attributes. Any of these methods may provide morphometric information regarding cells. Such information may be measured quantitatively. In some embodiments, for quantitative microscopy, a sample is analyzed by two or more of quantitative fluorescence microscopy, quantitative dark field microscopy, quantitative bright field microscopy, and quantitative phase contrast microscopy. Quantitative microscopy may include use of image analysis techniques and/or statistical learning and classification methods to process images obtained by microscopy.

Multiple different cellular attributes may be measured by during quantitative microscopy. Cellular attributes that may be measured include, without limitation:

Physical attributes: e.g. cell size, volume, conductivity, low and high angle scatter, and density.

Morphological attributes: e.g. cell shape, area, size, and lobularity; nucleus shape area, size, and lobularity; mitochondria shape, area, size, and lobularity; and ratio of nuclear volume to cell volume.

Intracellular attributes: e.g. nucleus centroid/cell centroid distance (i.e. distance between the center of the nucleus and the center of the cell), nucleus lobe centroid distance (i.e. distance between the center of different lobes of the nucleus), distribution of proteins with the cells (e.g. actin, tubulin, etc.), and distribution of organelles within the cells (e.g. lysosomes, mitochondria, etc.).

Biochemical attributes: e.g. expression level of cellular proteins, cell surface proteins, cytoplasmic proteins, nuclear proteins, cellular nucleic acids, cell surface nucleic acids, cytoplasmic nucleic acids, nuclear nucleic acids, cellular carbohydrates, cell surface carbohydrates, cytoplasmic carbohydrates, and nuclear carbohydrates.

In some embodiments, methods, systems, and devices are provided herein for the quantitative measurement of two, three, four, five or more attributes of cells in a sample, wherein the attributes are selected from physical attributes, morphological attributes, intracellular attributes, and biochemical attributes. In some embodiments, methods, systems, and devices are provided herein for the quantitative measurement of two, three, four, five or more attributes of cells in a sample, wherein the attributes are selected from: cell size, cell volume, cell conductivity, cell low angle light scatter, cell high angle light scatter, cell density, cell shape, cell area, cell lobularity, nucleus shape, nucleus area, nucleus size, nucleus lobularity, mitochondria shape, mitochondria area, mitochondria size, mitochondria lobularity, ratio of nuclear volume to cell volume, nucleus centroid/cell centroid distance, nucleus lobe centroid distance, distribution of proteins with the cells (e.g. actin, tubulin, etc.), distribution of organelles within the cells (e.g. lysosomes, mitochondria, etc.), expression level of a cellular protein, expression level of a cell surface protein, expression level of a cytoplasmic protein, expression level of a nuclear protein, expression level of a cellular nucleic acid, expression level of a cell surface nucleic acid, expression level of a cytoplasmic nucleic acid, expression level of a nuclear nucleic acid, expression level of a cellular carbohydrate, expression level of a cell surface carbohydrate, expression level of a cytoplasmic carbohydrate, and expression level of a nuclear carbohydrate.

In some embodiments, methods are provided for the quantitative measurement of two, three, four, five, or more attributes of cells in a biological sample by microscopy, wherein the method may include one or more of the following steps or elements. The attributes of the cells quantitatively measured may be selected from the attributes listed in the immediately above paragraph. The biological sample may be pre-treated prior to microscopy. Pre-treatment may include any procedure to aid in the analysis of the sample by microscopy, including: treatment of the sample to enrich for cells of interest for microscopy, treatment of the sample to reduce components in the sample which may interfere with microscopy, addition of material to the sample to facilitate analysis of the sample by microscopy (e.g. diluents, blocking molecules to reduce non-specific binding of dyes to cells, etc.). Optionally, prior to microscopy, a sample may be contacted with one or more binders that specifically bind to a cellular component. Binders may be directly linked to a dye or other particle for the visualization of the binder. A sample may also be contacted with a secondary binder, which binds to the binder which binds to the cellular component. A secondary binder may be directly linked to a dye or other particle for the visualization of the binder. Prior to microscopy, a sample may be assayed in a spectrophotometer. For microscopy, a biological sample containing or suspected of containing an object for microscopic analysis may be introduced into a sample holder, such as a slide or a cuvette. The sample holder containing a sample may be introduced into a device configured to perform quantitative microscopy on the sample. The microscope may be coupled with an image sensor to capture images generated through the microscope objective. In the device, multiple images of the sample may be acquired by microscopy. Any one or more of quantitative fluorescence microscopy, quantitative dark field microscopy, quantitative bright field microscopy, and quantitative phase contrast microscopy may be used to obtain images of the sample. Optionally, images of the entire sample in the sample holder may be acquired by microscopy. Multiple fields of view of the microscope may be required capture images of the entire sample in the sample holder. The sample holder may move relative to the microscope or the microscope may move relative to the sample holder in order to generate different field of views in order to examine different portions of the sample in the sample holder. Multiple images of the same field of view of the sample in the sample holder may be acquired. Optionally, multiple filters may be used with the same type of microscopy and the same field of view of the sample, in order to acquire different images of the same sample which contain different information relating to the sample. Filters that may be used include, without limitation band-pass and long pass filters. Filters may permit the passage of certain wavelengths of light, and block the passage of others. Optionally, multiple types of microscopy (e.g. fluorescence, dark field, bright field, etc.) may be used to acquire images of the same field of view of the sample, in order to acquire different images of the same sample which contain different information relating to the sample. Optionally, video may be used to collect microscopy images. Optionally, microscopy images may be collected in 3-D. For microscopy performed as described herein, the device or system may be configured to link information relating to a cell in one image of the sample to the same cell in a different image of the sample. Based on different images of the same sample and/or same cells, multiple attributes of cells in the sample may be determined. In some aspects, the combination of multiple attributes/multiple pieces of information about cells in a sample may be used to reach a clinical decision and/or to draw a conclusion about the cells that would not be possible based on information from only a single attribute of the cells.

In some embodiments, devices and systems are provided for the quantitative measurement of two, three, four, five, or more attributes of cells in a biological sample by microscopy. In some embodiments, the device or system contains both a microscope or cytometer and a spectrophotometer. The device or system may further contain a fluid handling apparatus, which is configured to move sample between a spectrophotometer and a microscope or cytometer. In some embodiments, devices and systems for performing the methods disclosed herein are configured as described in U.S. patent application Ser. No. 13/244,947, which is hereby incorporated by reference in its entirety.

Dynamic Dilution

In some embodiments, methods, systems, and devices are provided herein for dynamic dilution of cell-containing samples.

In one embodiment, a method for dynamic dilution of a sample may include one or more of the following steps or elements. One or more stains may be added to a biological sample containing cells. The mixture of stain and sample may be incubated. The cells in the mixture of stain and sample may be washed to remove excess (unbound) stain. The stained, washed cells may be prepared in a desired volume for further analysis. The stained, washed cells may be analyzed to determine the approximate number or concentration of cells in the sample or a portion thereof. Based on the number or concentration of stained cells in the sample or portion thereof, a volume of sample may be obtained for further analysis, such that a desired number or concentration of cells for further analysis is obtained.

In some embodiments, samples may be diluted as described in U.S. patent application Ser. No. 13/355,458, which is hereby incorporated by reference in its entirety.

Dynamic Staining

In some embodiments, methods, systems, and devices are provided herein for dynamic staining of cell-containing samples.

Measurement of a Component of Interest in Cells of a Cellular Population

In one embodiment, a method for dynamically staining a cell sample relates to a method for the measurement of a component of interest in cells of a cellular population in a sample.

As used herein, a "component of interest" refers to any type of molecule that may be present in a cell. "Components of interest" include proteins, carbohydrates, and nucleic acids. Typically, a "component of interest" is a specific species of molecule, such as a particular antigen. Non-limiting examples of "components of interest" of a cell include: CD5 protein, CD3 protein, etc.

As used herein, a "cellular population" refers to any grouping of cells, based on one or more common characteristics. A "cellular population" may have any degree of breadth, and may include a large number of cells or only a small number of cells. Non-limiting examples of "cellular populations" include: red blood cells (RBCs), white blood cells, B-cells, CD34+ B-cells, etc.

In some circumstances, it may be desirable to quantitatively measure a component of interest in cells of a certain cellular population in a sample from a subject. For example, it may be desirable to measure the extent of CD5 (the "component of interest") expression in B-cells (the "cellular population") in a sample of cells from a subject having chronic lymphocytic leukemia. Detection and/or measurement of the level of a component of interest may involve use of a binder molecule that has affinity for the specific component of interest, such an antibody or single chain variable fragment ("scFv"). In order to accurately measure the level of a specific component of interest in cells in a method involving the use of a binder molecule, it may be advantageous to expose the cells to the binder molecule at a specific ratio or range of ratios of binder molecule to target component of interest. For example, it may be desirable to provide an amount of binder to a collection of cells such that there is a linear relationship between the amount of component of interest in the cells and the amount of binder which binds to the component of interest in the cells. For example, it may be undesirable to have too little binder (such that there is not enough binder to bind to all of the components of interest in the cells) or to have too much binder (such that the binder binds non-specifically to the cells).

Using traditional methods, it may be difficult to provide an appropriate level of binder to a sample in order to accurately measure the amount of component of interest in a cellular population in the sample, due to the fact that the size of the cellular population and/or component of interest in the sample may vary significantly between different samples. In contrast, provided herein are methods, devices, and systems for dynamically staining cell samples to accommodate samples containing a wide range of cellular populations and components of interest.

In one embodiment, a method for the measurement of a component of interest in cells of a cellular population in a sample is provided. The method is not limited to but may include one or more of the following steps.

First, a quantitative or semi-quantitative measurement of a marker present in cells of the cellular population may be obtained. The marker may be any marker which is present in the cellular population of interest, and it may be a marker exclusively present in the cellular population of interest (i.e. not present in any other cell types in the sample). Measurement of the marker may be by any method, provided the method does not destroy the sample, and may use any system or device. A binder which recognizes the marker may be mixed with the sample. The binder may have a molecule attached to facilitate detection of the binder (e.g. a fluorescent marker). In an example, the marker may be detected and/or measured by fluorescence spectrophotometry. In embodiments in which the binder has a fluorescent label and the marker is measured by fluorescence spectrophotometry, fluorescence spectrophotometry may be used to measure a bulk fluorescence from the sample or a portion thereof, rather than to measure fluorescence from individual cells.

Second, based on the quantitative or semi-quantitative measurement of the marker present in cells of the cellular population, an approximate amount or concentration of cells of the cellular population present in the sample may be determined. The approximate number or concentration of cells in the cellular population present in the sample may be determined, for example, through the use of a calibration curve. Calibration curves may be prepared and/or may be available for different markers/binder combinations. Calibration curves may be developed, for example, by measuring the signal from known numbers of cells having a certain marker and bound with a certain binder. In some embodiments, the approximate amount or concentration of cells of the cellular population present in the sample may be determined with the aid of a computer. In some aspects, the approximate number or concentration of cells in the cellular population present in the sample may be determined at no more than about 10, 20, 30, 40, 50, 60, 70, 80, 90, 100, 150, 200, 250, 300, 400, or 500% off the true concentration.

Third, based on the determined amount or concentration of cells in the cellular population present in the sample, an amount of a reagent to add to the sample may be selected, wherein the reagent binds specifically to the component of interest in cells of the cellular population. The reagent may be any molecule that binds specifically to the component of interest. For example, the reagent may be a binder, such as an antibody. The reagent may be configured such that it may be readily detected (e.g. by fluorescence or luminescence) and/or such that under at least some circumstances, it produces a detectable signal. In some embodiments, the reagent may be attached to a molecule to facilitate detection of the reagent. The amount of reagent added to the sample may be any amount. In some embodiments, an amount of reagent may be added to the sample such that there is an approximately linear relationship between the level of the component of interest in individual cells of the cellular population and the signal produced by the reagents bound to the components of interest in individual cells of the cellular population.

Fourth, after the amount of a reagent to add to the sample is selected, the selected amount of reagent may be added to the sample.

Fifth, cells in the sample may be assayed for reagent bound to the compound of interest.

Sixth, based on the amount of reagent bound to the component of interest, the amount of the component of interest in cells of the cellular population of the sample may be determined.

In some embodiments, the fifth and sixth steps may be performed together such that the measurement of the amount of reagent bound to the component of interest is sufficient to identify the amount of the component of interest in cells of the cellular population of the sample.

In other embodiments, provided herein are systems and devices for the dynamic staining of samples. The systems and devices may contain, without limitation, a spectrophotometer and a fluorescence microscope. In an embodiment, a system or method for dynamic staining of samples may be configured as described in U.S. patent application Ser. Nos. 13/244,947 or 13/355,458, which are hereby incorporated by reference in their entirety. In an embodiment, the systems and devices may be automated to determine an amount of a reagent to add to a sample to determine the amount of a component of interest in cells of a cellular population in a sample, based on a measurement of an amount of a marker present in cells of the cellular population. In another embodiment, the systems and devices may be automated to determine an amount of a reagent to add to a sample to determine the amount of a first component in cells of a cellular population in a sample, based on a measurement of an amount of a second component in the cells of the cellular population in a sample.

Context-Based Autofocus

In some embodiments, methods, systems, and devices are provided herein for context-based microscopy autofocus.

The length of many clinically relevant objects in biological samples spans a wide range. For example, bacteria are commonly about 1 µm in length, erythrocytes are commonly about 6-8 µm in length, leukocytes are commonly about µm 10-12 in length, epithelial cells may be about 100 µm in length, and cast and crystals may be about 200-300 µm in length. In addition, there are many amorphous elements such as urinary mucus which exist as strands or filaments which may range from about 10-400 µm in length.

A challenge in microscopy is to acquire precise images of fields of view that contain an unknown and arbitrary composition of objects of various sizes, such as those described above. Since the depth of focus of many microscopy objectives is limited (typically about 1-10 µm), for a given field of view containing elements of various sizes, multiple focal planes for the given field of view may need to be acquired in order to obtain accurate sharp images of the various elements within the field of view. A problem with many traditional autofocus methods is that they are designed to focus on the dominant feature in a field of view, so that the sharpness of that feature can be maximized. Such methods may be ineffective for capturing elements of various sizes in a sample.

In one embodiment, a method is provided for context-based microscopy autofocus, which includes mixing a reference particle of a known size with a sample for microscopy. The reference particle may be detected during microscopy, and used to achieve focusing. By use of the reference particles to achieve focusing, focal planes may be selected independent from the overall image composition. In one aspect, the method may be useful to achieve focusing on a sample having an unknown composition of elements. In another aspect, the method may support the generation of precise planes of focus, independent of the precision of the microscope or microscopy-related hardware. For example, when a plane of focus is selected based on feedback from the sharpness of the reference particles within a field of view, precise focusing on various elements within a sample may be achieved, regardless of the level of accuracy or precision of the focusing hardware [e.g. the microscope objective actuation, the shape of a sample holder (e.g. a cuvette or slide), or the non-uniformity of a sample holder].

In an embodiment, a reference particle may contain or be labeled with a molecule to facilitate detection of the particle during microscopy. In one example, a reference particle may be labeled with or contain a fluorescent molecule. The fluorescent molecule may absorb light at a first wavelength of light, and, in response to the absorbance of the first wavelength of light, it may emit light at a second wavelength. In an embodiment, a sample mixed with a reference particle may be exposed to a wavelength of light capable of exciting a fluorescent molecule in a reference particle of interest and emitted light from the fluorescent molecule may be measured. Specific fluorescence from a reference particle may be used to detect reference particles, and information from detected reference particles in a sample may be used for autofocusing.

Reference particles may be of any shape, such as spherical or cuboid. Reference particles include, without limitation, beads and microspheres. Reference particles may be of any size, such as with a diameter or length of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 20, 30, 40, 50, 60, 70, 80, 90, 100, 125, 150, 175, 200, 250, 300, 350, 400, 450, or 500 µm. Reference particles may contain any material, such as polystyrene, polystyrene, latex, acrylic, or glass.

In one embodiment, a method for focusing a microscope is provided, which may include one or more of the following steps. First, a sample containing an object for microscopic analysis (e.g. bacteria, erythrocytes, etc.) may be mixed with a reference particle. The reference particle may contain or be labeled with a molecule to facilitate the detection of the particle, such as a fluorophore. Second, the mixture containing the reference particle and the sample may be positioned into a light path of a microscope, for example in cuvette or slide. Optionally, the reference particle may sink to the bottom of the sample in the cuvette or slide, such that the reference particle rests on the lowest surface of the cuvette or slide which is in contact with the sample. The microscope may be of any type, including a fluorescent microscope. Third, the mixture may be exposed to a light beam configured to visualize the reference particle. The light beam may be of any type, and may be of any orientation relative to the reference particle. For example, the light beam may be at a wavelength capable of exciting a fluorophore within or attached to the reference particle. Exposure of the reference particle to the light beam may result in, for example, the generation and emission of light at a particular wavelength from the reference particle and/or scattering of light from the reference particle. Fourth, light emitted or scattered from the reference particle may be detected by the microscope, and this information may be used in order to determine the position of the reference particle within the mixture and/or to focus the microscope. Optionally, the microscope may be focused into a plane of focus suited for objects of similar size to the reference particle. An image from the microscope may be obtained by an image sensor. The image may be saved and/or or used for image analysis.

In some embodiments, a plurality of reference particles may be added to a sample. The reference particles may be all of the same size, or they may be of different sizes. In some embodiments, reference particles of different sizes contain different fluorophores. Different fluorophores may have different absorption wavelengths, different emission wavelengths, or both.

In an embodiment, a method for focusing a microscope is provided, including mixing more than one reference particle of known size with a sample for microscopy, wherein at least two of the reference particles are of different sizes and contain different fluorophores. The method may include one or more of the following steps. First, a sample containing an object for microscopic analysis may be mixed with two or more reference particles, wherein at least two of the reference particles are of different sizes and contain different fluorophores (i.e. the "first reference particle" and the "second reference particle"). Second, the mixture containing the reference particles and the sample may be positioned into the light path of a microscope. The microscope may be of any type, including a fluorescent microscope. Third, the mixture may be exposed to a light beam configured to visualize the first reference particle. The light beam may be of any type, and may be of any orientation relative to the first reference particle. For example, the light beam may be at a wavelength capable of exciting a fluorophore within or attached to the first reference particle. Exposure of the first reference particle to the light beam may result in the generation and emission or scattering of light at a particular wavelength from the first reference particle. Fourth, light emitted or scattered from the first reference particle may be detected, and this information may be used in order to determine the position of the first reference particle within the mixture and/or to focus the microscope into a first plane of focus suited for objects of similar size to the first reference particle. Optionally, an image of the first focal plane may be obtained by an image sensor. The image may be saved and/or or used for image analysis. Fifth, the mixture may be exposed to a light beam configured to visualize the second reference particle. The light beam may be of any type, and may be of any orientation relative to the second reference particle. Exposure of the second reference particle to the light beam may result in the generation and emission or scattering of light at a particular wavelength from the second reference particle. Sixth, light emitted or scattered from the second reference particle may be detected, and this information may be used in order to determine the position of the second reference particle within the mixture and/or to focus the microscope into a second plane of focus suited for objects of similar size to the second reference particle. Optionally, an image of the second focal plane may be obtained by an image sensor. The image may be saved and/or or used for image analysis.

In other embodiments, provided herein are systems and devices for context-based microscopy autofocus. The systems and devices may contain, without limitation, a fluorescence microscope. In an embodiment, the systems and devices may be automated to add a reference particle having a known size to a sample for microscopic analysis to form a mixture, to position the mixture into the light path of a microscope, to expose the mixture to a light beam configured to visualize the reference particle, to determine the position of the reference particle within the mixture and/or to focus the microscope based on the position of the reference particle within the mixture. In an embodiment, a system or method for context-based microscopy autofocus may be configured as described in U.S. patent application Ser. Nos. 13/244,947 or 13/355,458, which are hereby incorporated by reference in their entirety.

Cell Counting/Enumerating Cells

In some embodiments, methods, systems, and devices are provided herein for enumerating cells in a sample.

Certain traditional methods for staining cell-containing samples involve staining a specific volume of a sample (e.g. blood) with a particular concentration or amount of stain. This may be referred to as "volumetric staining" Volumetric staining has a number of shortcomings, including: (i) it fails to address normal variations in cell subpopulations between different subjects (e.g. different healthy subjects may have widely different numbers of subpopulations of cells, such as CD3+ T cells) and (ii) it fails to address that pathological samples may have dramatically different cellular composition when compared to healthy samples (e.g. the percent and number of CD3+ T cells in blood are greatly elevated in patients with T cell leukemia over the percent and number in healthy subjects).

For accurate and reproducible staining of cell-containing samples, it may be desirable to add a specific amount of a cellular stain (e.g. DNA dyes, antibodies, binders, etc.) to a specific number or concentration of cells. For example, it may be desirable to add 0.2 micrograms of a particular stain for white blood cells per 1000 white blood cells in a sample. After an incubation period of the dye with the cells, a sample may be washed to remove excess (unbound) dye, prepared to an appropriate cell density for microscopy, and imaged. In this manner, a stain and staining procedure can be optimized or normalized for a particular cell number.

In one embodiment, a method is provided for enumerating the number of cells in a sample. The method may include one or more of the following steps or elements. A first stain that will bind to the cells of interest in a sample may be added to the sample. The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. Based on the number of cells in the sample, a second stain that will bind to cells of interest in a sample may be added to the sample. The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed by microscopy.

Enumerating Cells in a Sample Prior to Determining the Ploidy of Cells

In one embodiment, a method for enumerating cells in a sample prior to determining the ploidy of the cells is provided, wherein the method includes one or more of the following steps or elements. A first stain which binds to the cells of interest in the sample and that is spectrally distinct from the emission of a DNA dye may be added to the sample. The cells of interest may be, for example, white blood cells. The first stain may be, for example, a fluorphore-conjugated antibody. A fluorphore-conjugated antibody may bind to, for example, a widely expressed antigen (e.g. CD45), or it may bind to an antigen expressed by a specific sub-population of cells (e.g. CD3 for T cells). The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. Based on the number of cells in the sample, a second stain that will bind to cells of interest in a sample may be added to the sample. The second stain may be a DNA dye, such as propidium iodide or 4',6-diamidino-2-phenylindole ("DAPI"). The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed for ploidy by microscopy.

In methods for determining the ploidy of cells, it may be important to combine a given number of cells for ploidy analysis with a certain amount or concentration of DNA stain, in order to generate accurate and consistent data regarding the ploidy of the cells. In one example, the number of white blood cells per volume of blood may vary within a healthy population, and thus, it may be desirable to determine the number of white blood cells in a volume of blood before attempting to stain the white blood cells for ploidy analysis.

The methods provided above for determining the ploidy of cells may also be performed for any method in which enumerating cells in a sample prior to determining an attribute related to the nucleic acid content of a cell is desired. For example, the above method may be used with methods involving enumerating cells in a sample prior to determining the morphology of nuclei of cells, the size of the nuclei of cells, the ratio of nuclei area to total cell area, etc.

Enumerating Cells in a Sample Prior to Cell Surface Staining

In one embodiment, a method for enumerating cells in a sample prior to cell surface staining is provided, wherein the method includes one or more of the following steps or elements. A first stain which binds to the cells of interest in the sample and that is spectrally distinct from the emission of a dye to be used to stain the surface of the cells of interest may be added to the sample. The cells of interest may be, for example, white blood cells. The first stain may be, for example, a DNA dye (e.g. propidium iodide or DAPI). The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. Based on the number of cells in the sample, a second stain that will bind to cells of interest in a sample may be added to the sample. The second stain may be, for example, a fluorphore-conjugated antibody. A fluorphore-conjugated antibody may bind to, for example, a widely expressed antigen (e.g. CD45), or it may bind to an antigen expressed by a specific sub-population of cells (e.g. CD3 for T cells). The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed for a cell surface antigen by microscopy.

In methods for cell surface antigen staining of cells, it may be important to combine a given number of cells for analysis with a certain amount or concentration of cell surface antigen stain, in order to generate accurate and consistent data regarding the content of the cell surfaces. In one example, the number of white blood cells per volume of blood may vary within a healthy population, and thus, it may be desirable to determine the number of white blood cells in a volume of blood before attempting to stain the white blood cells for cell surface antigens. In another example, the number of white blood cells per volume of blood may vary between healthy and sick subjects, and thus, it may be desirable to determine the number of white blood cells in a volume of blood before attempting to stain the white blood cells for cell surface antigens. As a theoretical example, a healthy patient may have 100 cells per microliter of blood, and 10 of these are CD3+ T cells, while a lymphoma patient may have 1000 cells per microliter of blood and 900 of these are CD3+ T cells. If 100 microliters of blood is traditionally stained, then a sample from a healthy subject would contain 10,000 total cells/1000 CD3+ T cells, and a sample from a lymphoma subject would contain 100,000 total cells/90,000 CD3+ T cells. In this theoretical example, the pathological sample contains ten times the number of total cells and ninety times the number of CD3+ T cells, when compared to a sample from a healthy subject. If the pathological sample would be stained with a traditional "volumetric staining" approach that is optimized for samples from healthy subjects, the sample from the lymphoma subject may be insufficiently stained.

Accordingly, methods provided herein may be used to enumerate cells in a sample before cell staining, in order to generate accurate and/or consistent data regarding samples.

Method Speeds

Methods, systems, and devices provided herein may support the rapid development of sample analysis results. Any of the methods provided herein may provide analysis results in less than about 6 hours, 4 hours, 3 hours, 2 hours, 1 hour, 45 minutes, 30 minutes, 15 minutes, 10 minutes, or 5 minutes from the initiation of the method.

Rapid analysis results may be used to provide real-time information relevant to the treatment, diagnosis, or monitoring of a patient. For example, rapid analysis results may be used to guide a treatment decision of a surgeon operating on a patient. During surgery, a surgeon may obtain a biological sample from a patient for analysis. By receiving rapid analysis of a sample by a method provided herein, a surgeon may be able to make a treatment decision during the course of surgery.

In another example, rapid analysis results provided by the methods, systems, and devices provided herein may support a patient receiving information regarding a biological sample provided by the patient at a point of service during the same visit to the point of service location in which the patient provided the biological sample.

Analysis of Pathology Samples

Any of the methods provided herein may be used to analyze cell-containing pathology samples. If a pathology sample is a tissue sample, the sample may be treated to separate the cells of the tissue into individual cells for analysis by methods provided herein.

Analysis of pathology samples by any of the methods provided herein may support rapid pathology analysis, and the rapid integration of pathology analysis results into a treatment decision for a patient.

Additional Procedures in Response to Analysis Results

In some embodiments, the devices and systems provided herein may be configured to trigger an additional procedure in response to a result obtained by an analysis method provided herein.

In one example, a device or system may be programmed to provide an alert to a user if a result is outside of an expected range. The alert may prompt a user or medical personnel to, for example, manually analyze a sample, check the device or system for proper operation, etc.

In another example, a device or system may be programmed to automatically run one or more additional tests on a sample if a result is within or outside of a certain range. In some examples, devices and systems provided herein are capable of performing multiple different assays, and the device or system may run an addition assay to verify or further investigate a result generated by a method provided herein.

EXAMPLES

Example 1

A sample of cells containing blood leukocytes including natural killer cells and neutrophils was obtained. The sample was treated with a fluorescently labeled identity binder (anti-CD16 binder), which binds to both natural killer cells and neutrophils. The sample was also treated with a nuclear dye (DRAQ5). The sample was imaged by fluorescence microscopy and dark field microscopy. The level of fluorescence and light side scatter of different cells in the sample was recorded and analyzed. Segmented images containing the anti-CD16 binder signal provided quantitative information on the fluorescence intensity of each cell (corresponding to the CD16 expression level), and also the size of each cell. The darkfield image provided quantitative information on the scatter properties of each cell. Images containing the DNA dye signal were segmented to determine the fluorescent intensity, size, and shape of the nucleus.

Figure 1B:
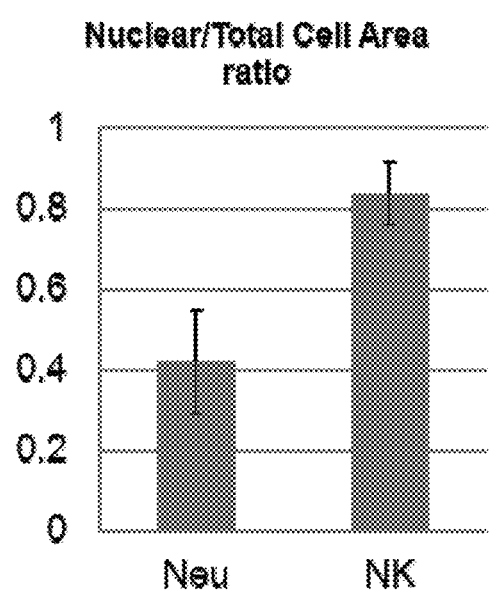
Figure 1C:
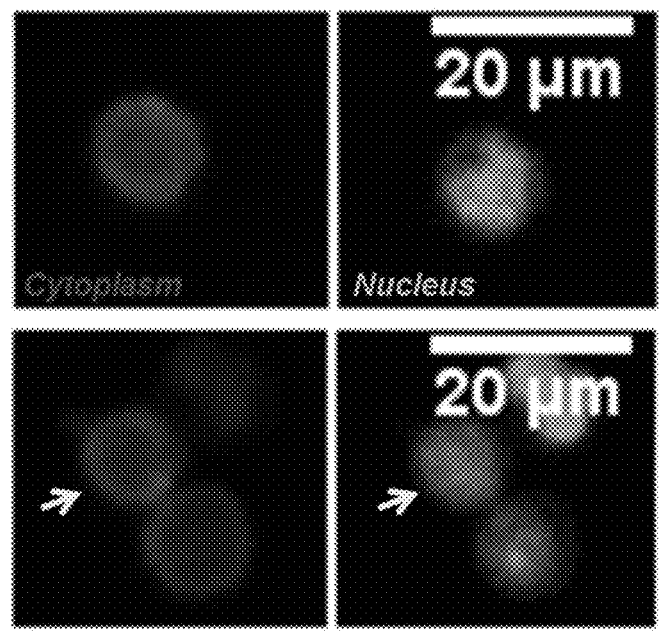
Figure 1D:
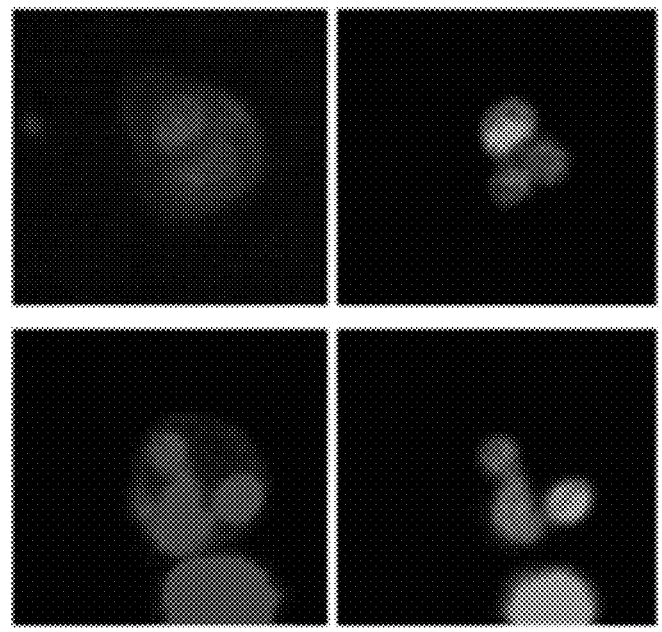

As shown in FIG. 1A, two major groupings cells were identified based on the measurement of CD16 fluorescence and light scatter of the different cells. The group of cells with bright/high CD16 fluorescence signal and high scatter (FIG. 1A, right circle) are neutrophils. The group of cells with intermediate CD16 fluorescence signal and low scatter (FIG. 1A, left circle) are natural killer cells. While the measurement of fluorescence and light scatter of the different cells provides enough information to classify most cells in the sample as either natural killer cells or neutrophils, for some cells, measurement of these attributes does not provide enough information to classify the cells with a high degree of accuracy. For example, the measurement of fluorescence and light scatter of cells does not provide enough information to accurately classify the small group of cells in the smallest circle in FIG. 1A (i.e. the middle circle). In order to identify whether the cells in the smallest circle were natural killer cells or neutrophils, images of the nuclear (DRAQ5) and total cell (anti-CD16) staining of these were examined. Quantitative measurements of the area of the nucleus and the total cell volume of the cells were obtained, and the ratio of nuclear area to total cell area was determined. As shown in FIG. 1B, there is a clear difference in the ratio of nuclear area to total cell area between natural killer cells ("NK") and neutrophils ("Neu"). Thus, the use of quantitative microscopy to examine multiple attributes of cells in the sample was used to allow for unambiguous classification of cells. FIG. 1C shows images of natural killer cells from the smallest circle in FIG. 1A. All images have the same length scale. The images on the left are cells stained for total cell area (anti-CD16), and the images on the right are the same cells with just nuclear staining (DRAQ5). The images on the top and bottom row are different examples of the natural killer cells. FIG. 1D shows images of neutrophils from the smallest circle in FIG. 1A. All images have the same length scale. The images on the left are cells stained for total cell area, and the images on the right are the same cells with just nuclear staining. The images on the top and bottom row are different examples of the natural killer cells.

In addition, the nucleus of a neutrophil has a distinctive multi-lobed shape, whereas the nucleus of a natural killer cell (and other lymphocytes) is round, even, and smooth. Image segmentation algorithms may be used to identify and classify cells based on the shape of the nucleus itself.

Example 2

Figure 2A:
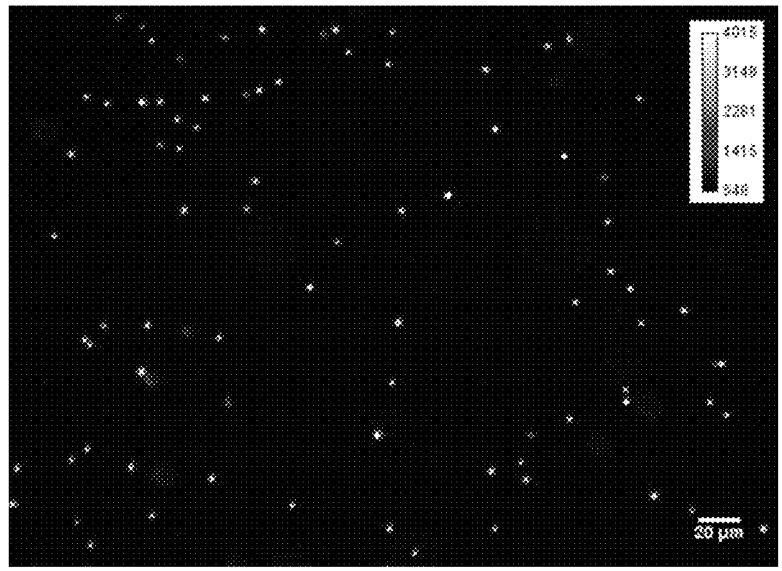
FIG. 2 shows: (A) platelets labeled with fluorescently conjugated CD41 and CD61 antibodies (bright dots); (B) intensity distribution of images of fluorescently labeled platelets at 10× (left) and 20× (right) magnification; (C) intensity distribution of an image of a fluorescently labeled platelet showing measured intensity (light grey) and curve fit to the measured intensity (dark grey).
Figure 2B:
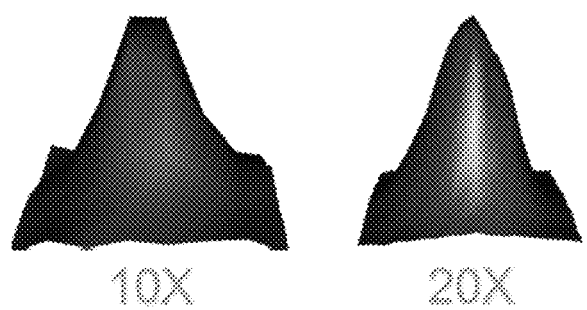
Figure 2C:
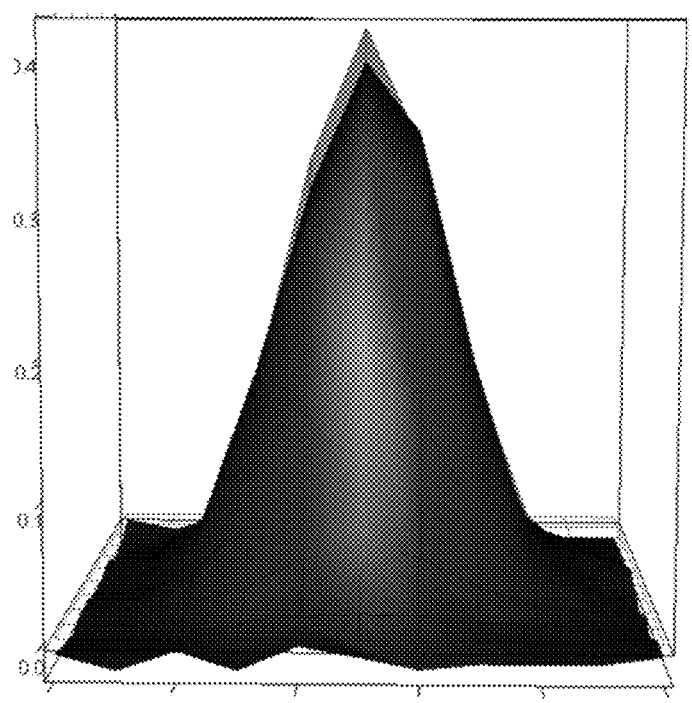

A sample containing platelets was obtained. The platelets were labeled with fluorescently conjugated anti-CD41 and anti-CD61 antibodies. Beads having a diameter of 3 μm were also added to the sample. The sample was imaged at 10× and 20× magnifications (FIG. 2A). The intensity of fluorescence distribution for individual platelets was measured (from both antibodies), and determined have a Gaussian shape (FIG. 2B). The measured values of fluorescence of individual platelets was plotted, and a fit for the intensity distribution was determined (FIG. 2C). In FIG. 2C, the grey line is the measured fluorescence intensity across an individual platelet, and the black line is the fit. Parameters of the fit, such as the mean of the Gaussian, the variance, the volume, the width, and the area of the base, etc., can be evaluated as predictors of platelet volume. The volume of the Gaussian and the width of the fit have been determined to correlate closely with mean platelet volume.

For the above measurements, the 3 μm beads served as references and fiducials for controlling variance in accurately determining the best plane of focus, and the effect of this variance on the measurement of volume.

Figure 3:
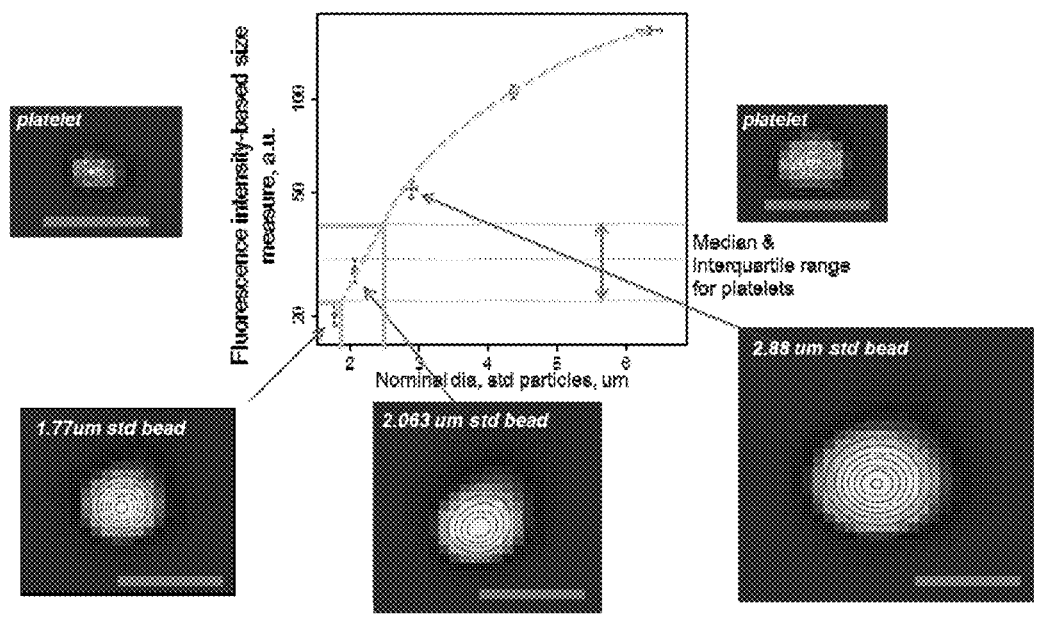
FIG. 3 shows: a plot of curve of showing the relationship between the nominal diameter of standard particles in μm (x-axis) and fluorescence intensity-based size measure in a.u. (y-axis). The figure also shows representative beads at different points along the curve.

In addition, platelet size estimated based on fitting a 2D model can be calibrated to be in the normal range (FIG. 3).

Example 3

Figure 4:
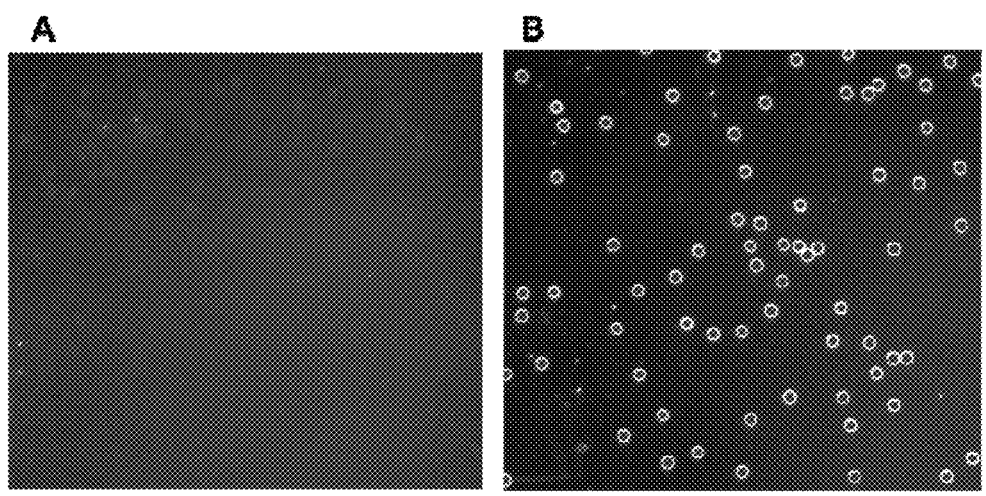
FIG. 4 shows: sphered red blood cells imaged by dark field microscopy in cuvettes that allow (A) only epi-illumination, and (B) a mixture of epi- and trans-illumination.

A sample containing red blood cells ("RBCs") was obtained. The RBCs were treated to swell the RBCs into a sphere-like shape, by treating the RBCs with a low concentration of a surfactant (DDAPS or SDS). The RBCs were imaged by dark field microscopy in two different cuvettes: (A) a cuvette that allowed only pure epi-illumination (FIG. 4A); and (B) a cuvette that allowed a mixture of both epi and trans-illumination (FIG. 4B). The RBCs were much more visible in the cuvette that allowed a mixture of both epi and trans-illumination over the cuvette that allowed only pure epi-illumination (FIG. 4).

Example 4

A sample containing neutrophils was obtained. In neutrophils, the shape and chromatin morphology of the nucleus may indicate whether it is an immature "band" neutrophil or a mature "segmented" neutrophil. Band neutrophils are immature neutrophils that have recently emerged from the bone marrow. An increase in the proportion of band neutrophils may indicate an ongoing infection or inflammation.

The sample was mixed with a fluorescently labeled anti-CD16 antibody, which recognizes CD16, a cell surface receptor on neutrophils. The sample was also stained with a fluorescent nuclear dye. The sample was imaged by fluorescence microscopy, to obtain both nuclear staining and CD16 staining data from the cells. Band neutrophils generally have similar expression levels of CD16 as mature segmented neutrophils, and thus cannot be distinguished by virtue of fluorescence intensity from CD16 staining alone.

Figure 5A:
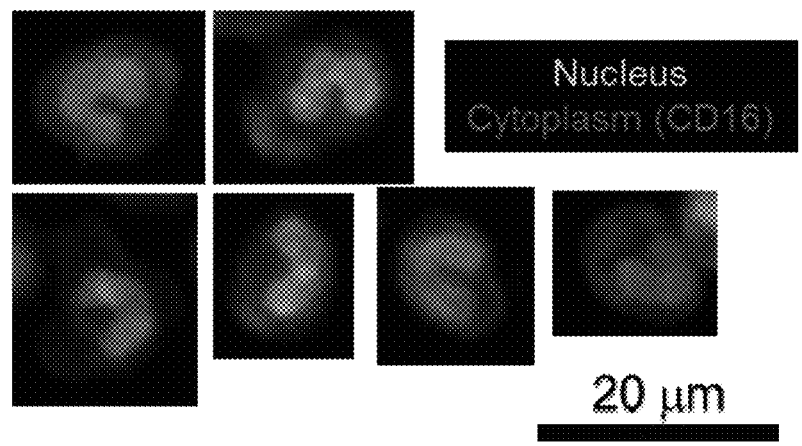
FIG. 5 shows: (A) putative band neutrophils stained with anti-CD16 antibody and a nuclear stain; (B) putative segmented neutrophils stained with anti-CD16 antibody and a nuclear stain.
Figure 5B:
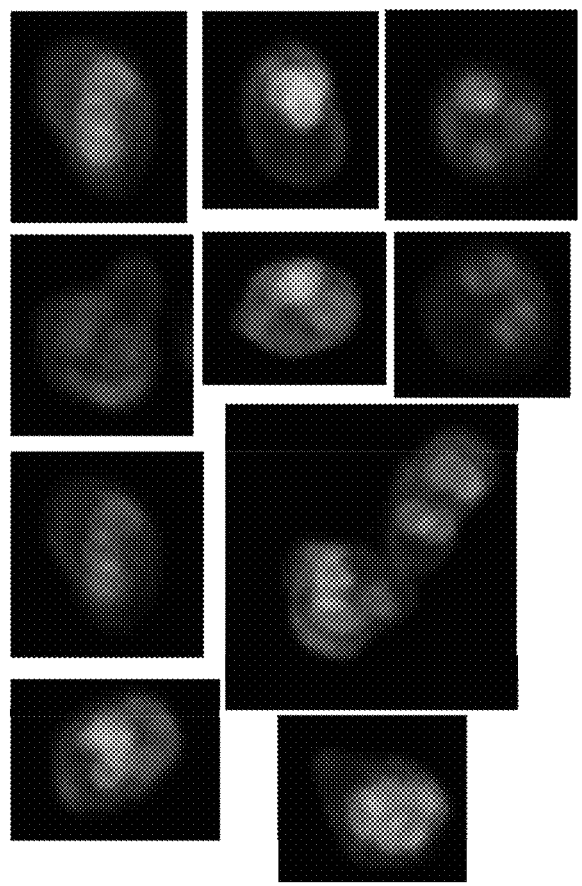

Image analysis including image segmentation is used to recognize nuclear staining and morphologies of band neutrophils and segmented neutrophils, thereby allowing classification of the cells. The size, shape, and fluorescence intensity of the nucleus of cells are examined. In addition, the nuclei are analyzed to determine the number of lobes (peaks in intensity within the nuclear area), distance between the lobes of the nucleus, and the changes in curvature (second derivative) of the nuclear outline. FIG. 5A shows representative images of band neutrophils. In these images, the nucleus appears as a light grey, and the cell cytoplasm appears as a darker grey. As neutrophils differentiate through the myeloid lineage, they develop a characteristic "U" shaped nucleus prior to reaching full maturity. FIG. 5B shows representative images of segmented neutrophils. In these images, the nucleus appears as a light grey, and the cell cytoplasm appears as a darker grey. The nuclei of segmented neutrophils have multiple segments/lobes (typically about 3-5). Thus, this analysis supports identification and quantification of different subpopulations of neutrophils in the blood.

Example 5

A sample of cells from a subject with chronic lymphocytic leukemia (CLL) is obtained. The objective is to quantify the extent of CD5 expression on B-cells from the subject. Anti-CD20 antibodies are selected as the binder for B-cells. Anti-CD20 antibodies labeled with a first colored fluorphore are mixed with the sample. After an appropriate incubation time, the sample is washed and the unbound anti-CD20 antibodies are removed. The sample is exposed to a light source capable of exciting the first fluorophore, and fluorescent signal is measured using a spectrophotometer. Based on the fluorescent signal, the approximate concentration of B-cells in the sample is determined. The determined approximate concentration of B-cells is, in fact, within 1.5 fold of the true concentration of B-cells in the sample. Based on the approximate concentration of B-cells in the sample, and appropriate amount of anti-CD5 binder to add to the sample so that a proportional relationship between CD5 expression and CD5 fluorescence is maintained is selected. The anti-CD5 binder is coupled to a second fluorophore, which has a different peak excitation wavelength than the first fluorophore (attached to the anti-CD20 binder). The anti-CD5 antibody is added to the sample, and then individual cells of the sample are exposed to a light source capable of exciting the second fluorophore, and fluorescent signal from individual cells is measured. Based on the fluorescent signal from cells, the average amount of CD5 in B-cells in the sample is determined.

Optical Systems

Figure 6:
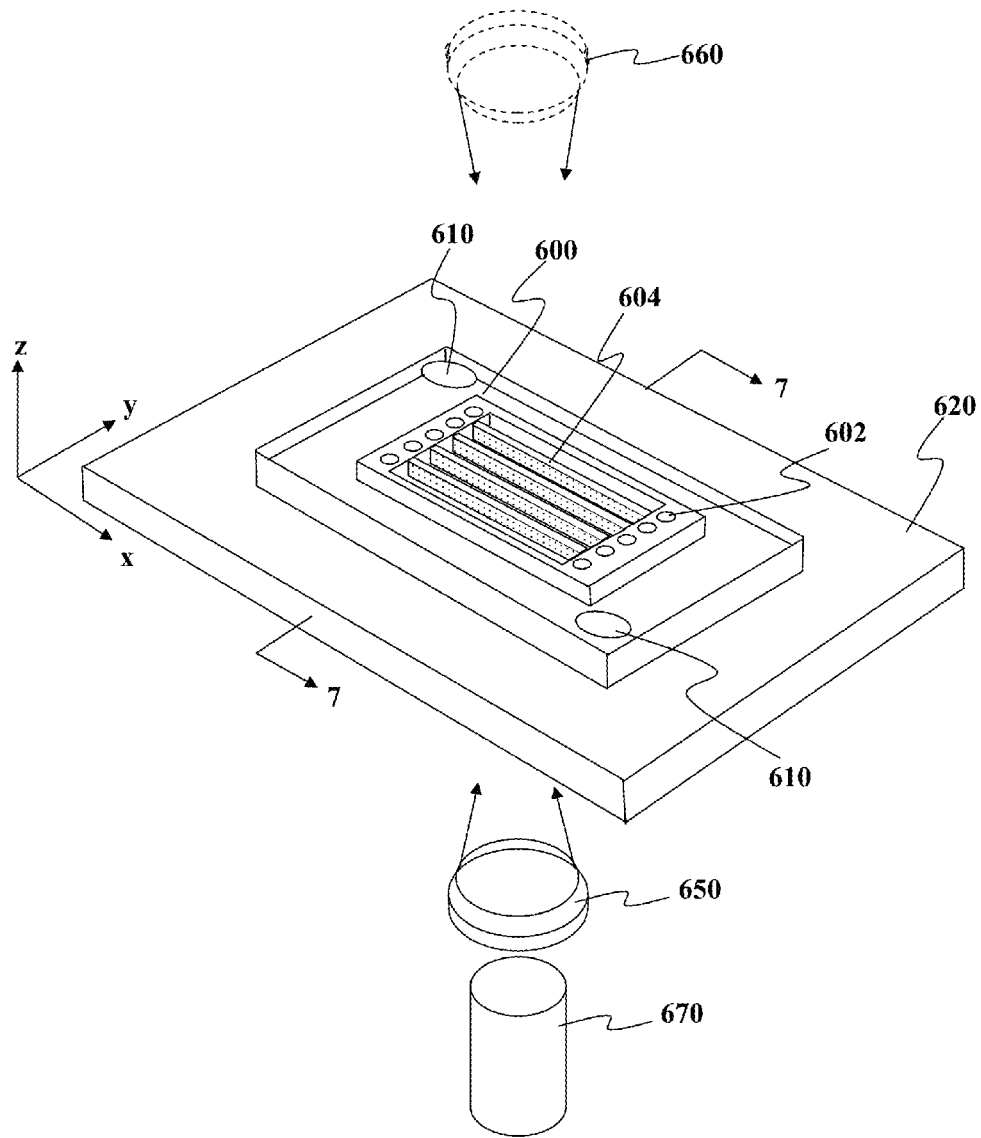
FIGS. 6-8 show various views of some embodiments of a sample imaging system.

Referring now to FIG. 6, one embodiment of an optical system suitable for use herein will now be described. Although this embodiment of the system is described in the context of being able to perform cytometry, it should also be understood that at least embodiments of the system also has capability beyond cytometry. By way of example and not limitation, the system can have application outside of cytometry due to the imaging and image processing capabilities associated with some embodiments. Since images are captured of the sample being analyzed and image information is typically linked or associated in the system to quantitative measurements, one can further analyze the images associated with the quantitative information to gather clinical information in the images that would otherwise be unreported.

The embodiment shown in FIG. 6 shows a perspective view of a cuvette 600 that has a plurality of openings 602 for receiving sample for analysis. Although the system is described in the context of a cuvette, it should be understood that other sample holding devices may also be used in place of or in combination with the cuvette 600.

As seen in the embodiment of FIG. 6, the openings 602 may allow for a sample handling system (not shown) or other deliver system to deposit sample into the opening 602 which may then lead to an analysis area in the cuvette where the sample can be analyzed. In one nonlimiting example, the analysis area may be a chamber. In another nonlimiting example, the analysis area may be a channel. In a still further nonlimiting example, the analysis area may be a channel wherein the sample is held in a non-flowing manner. In any of the embodiments herein, the system can hold the samples in a non-flowing manner during analysis. Optionally, some alternative embodiments may be configured to enable sample flow through the analysis area before, during, or after analysis. In some embodiments, after analysis, the sample is extracted from the cuvette 600 and then delivered to another station for further processing and/or analysis. Some embodiments may use gate(s) in the system to control sample flow.

FIG. 6 shows that some embodiments of cuvette 600 have a plurality of openings 602. Embodiments having more or fewer openings 602 in the cuvette 600 are not excluded. Some embodiments may link certain openings 602 such that select pairs or other sets of openings 602 can access the same channel. By way of nonlimiting example, there may an opening 602 at each end of an analysis area. Optionally, more than one opening 602 may be at one end of the analysis area.

Some embodiments may provide structures 604 over select areas of the cuvette 600. In one embodiment, the structures 604 are ribs that provide structural support for areas of the cuvette that are selected to have a defined thickness. The structures 604 may be use when the defined thickness areas are at a reduced thickness relative to certain areas of the cuvette and thus could benefit from mechanical support provided by structures 604.

In some embodiments, these controlled thickness areas are selected to be positioned over the analysis areas. In some embodiments, these controlled thickness areas can impart certain optical properties over or near the analysis areas. Some embodiments may configure the structures 604 to also impart optical properties on light passing through the cuvette 600. Optionally, some embodiments may configure the structures 604 to not have an impact on the optical qualities of the cuvette 600. In such an embodiment, the structures 604 may be configured to have one or more optically absorbent surfaces. For example and not limitation, certain surfaces may be black. Optionally, some embodiments may have the structures 604 formed from a material to absorb light. Optionally, the structures 604 can be positioned to provide mechanical support but do not interact with the optical properties of cuvette 600 near the analysis areas.

Some embodiments of cuvette 600 can be configured to have structures 610 that allow for a sample handling system to transport the cuvette 600. In one nonlimiting example, the structures 610 can be openings in the cuvette 600 that allow for a pipette or other elongate member to engage the cuvette 600 and transport it to the desired location. Optionally, in place of or in combination with said opening(s), the structures 610 can be a protrusion, hook, and/or other non-negative feature that can be used to engage a cuvette transport device.

It should be understood that the cuvette 600 is typically formed from an optically transparent or transmissive material. Optionally, only select portions of the cuvette 600 such as the analysis areas or areas associated with the analysis areas are optically transparent. Optionally, select layers or areas in the cuvette 600 can also be configured to be non-light transmissive.

FIG. 6 shows that in this embodiment, the cuvette 600 rests on a support structure 620 wherein at some or all of the support structure 620 is formed from an optically transparent or transmissive material. In some embodiments, the optically transparent or transmissive portions are configured to be aligned with the analysis areas of the cuvette 600 to allow for optical interrogation of the sample in the analysis area. In one nonlimiting example, the support structure 620 can be movable in the X, Y, and/or Z axis to move the cuvette 600 to a desired position for imaging. In one some embodiments, the support structure 620 comprises a platform or stage that moves only in two of the axes. Optionally, some support structures may move only in a single axis. The cuvette 600 can be configured to be operably coupled to the support structure 600 through friction, mechanical coupling, or by retaining members mounted to one or both of the components.

FIG. 6 further shows that for illumination for darkfield and/or brightfield observation, there may be an illumination source 650 such as but not limited to a ringlight below the support structure 620 to locate illumination equipment below the level of the cuvette 600. This leaves the upper areas of the cuvette 600 available for pipettes, sample handling equipment, or other equipment to have un-hindered access to openings or other features on a top surface of the cuvette 600. Optionally, some embodiment may locate an illumination source 660 (shown in phantom) above the cuvette 600 to be used in place of, in single, or in multiple combination with underside illumination source 650. An objective 670 can be positioned to observe the sample being illuminated. It should be understood that relative motion between the cuvette 600 and the optical portions 650 and 670 can be used to allow the system to visualize different analysis areas in the cuvette 600. Optionally, only one of components is in motion to interrogate different areas of the cuvette 600.

Figure 7:
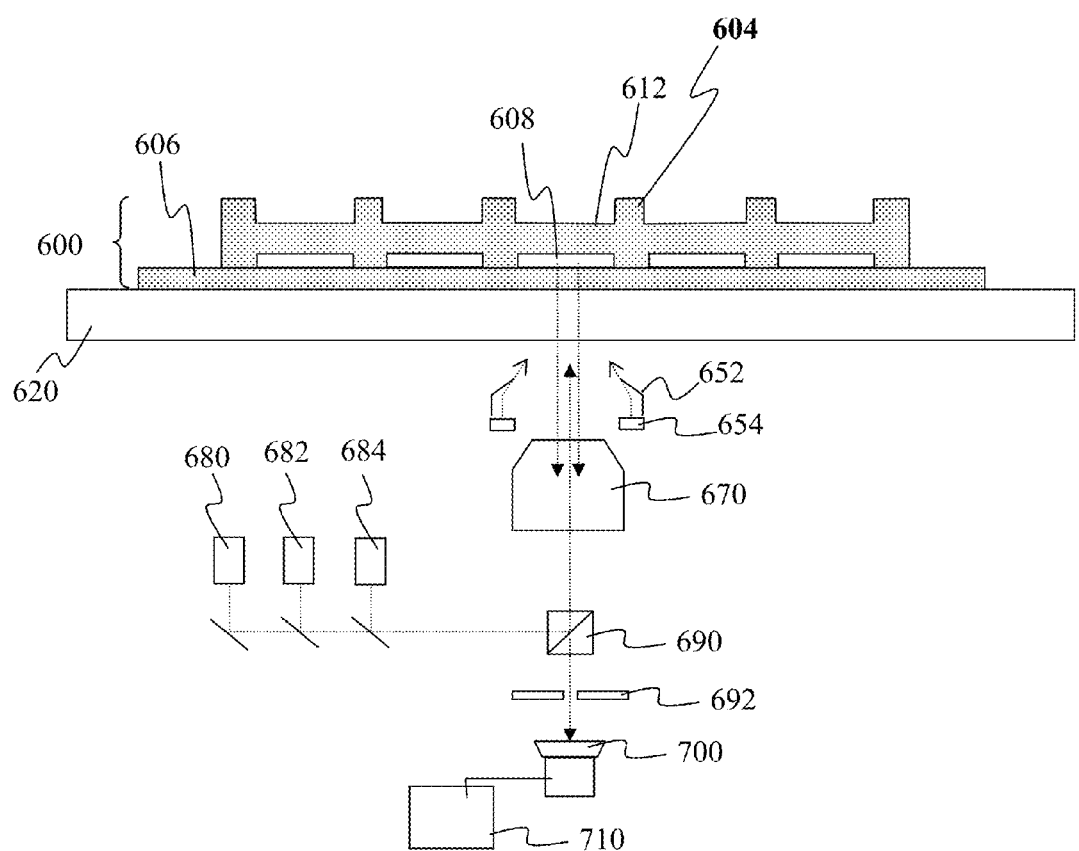

Referring now to FIG. 7, one embodiment of a suitable imaging system will now be described in more detail. FIG. 7 shows a schematic cross-sectional view of various components positioned below the support structure 620. The cross-section is along the area indicated by bent arrows 7 in FIG. 6.

FIG. 6 shows that in the present embodiment, the cuvette 600 comprises a base portion 606 and analysis areas 608 defined by a cover portion 612. Optionally, the analysis areas 608 may be defined within a single piece. Optionally, the analysis areas 608 may be defined by using more than two pieces, such as but not limited a discrete cover piece for each of the analysis areas 608. In one embodiment, the layer 606 comprises optically clear plastic such as but not limited to cyclo olefin polymer thermoplastic which deliver superior optical components and applications. Some may form one or more layers or components from glass, acrylic, clear polymer, or other transparent material.

In this nonlimiting example, the sample to be interrogated can be housed in whole or in part in the area 608. By way of non-limiting example, the optics below the support structure 620 may include a ringlight 650 that comprises a toroidal reflector 652 and a light source 654. Other illumination components suitable for darkfield illumination are not excluded. Some embodiments may use a mirror. Some embodiments use a coated reflective surface. Some embodiments may use a different reflector and not a toroidal reflection. Some embodiments may use a parabolic reflector. Some embodiments may use a parabolic reflector in the shape of an elliptic paraboloid. Some embodiments may use a plurality of individual reflector pieces. Some embodiments may not use any reflector. Some embodiments obtain oblique illumination through the use of angled light sources positioned to direct light with or without further assistance from one or more external reflectors.

The embodiment of FIG. 6 shows excitation energy sources 680, 682, and 684 such as but not limited laser diodes at specific wavelengths that are mounted to direct light into the sample in analysis area 608. In one nonlimiting example to facilitate compact packaging, the energy sources 680, 682, and 684 may direct light to a dichroic 690 that then directs the excitation wavelengths into the analysis area 608. The excitation wavelength(s) cause fluorescence wavelengths to be emitted by fluorophores in marker(s), dye(s), and/or other materials in the sample. The emitted fluorescence wavelengths are funneled through the objective 670, through the dichroic 690, through an optional filter wheel 692, and into a detector 700 such as but not limited to a camera system. By way of nonlimiting example, the dichroic 690 is configured to reflect excitation wavelengths but pass fluorescence wavelengths and any wavelengths desired for optical observation.

In one embodiment, all fluorescence excitation wavelengths are illuminating the sample in analysis area 608 simultaneously. The detector 700 may be coupled to a programmable processor 710 that can take the captured signal and/or image and deconstruct which wavelengths are associated with which fluorophores that are fluorescencing. Some embodiments may have the excitation sources illuminate the sample sequentially or in subsets of the entire number of excitation sources. Of course, it should be understood that the system is not limited to fluorescence based excitation and that other detection techniques and excitation techniques may be used in place of or in single or multiple combination with fluorescence. For example, some embodiments may also collect darkfield illumination scatter information simultaneously or sequentially in combination with fluorescence detection.

Figure 8:
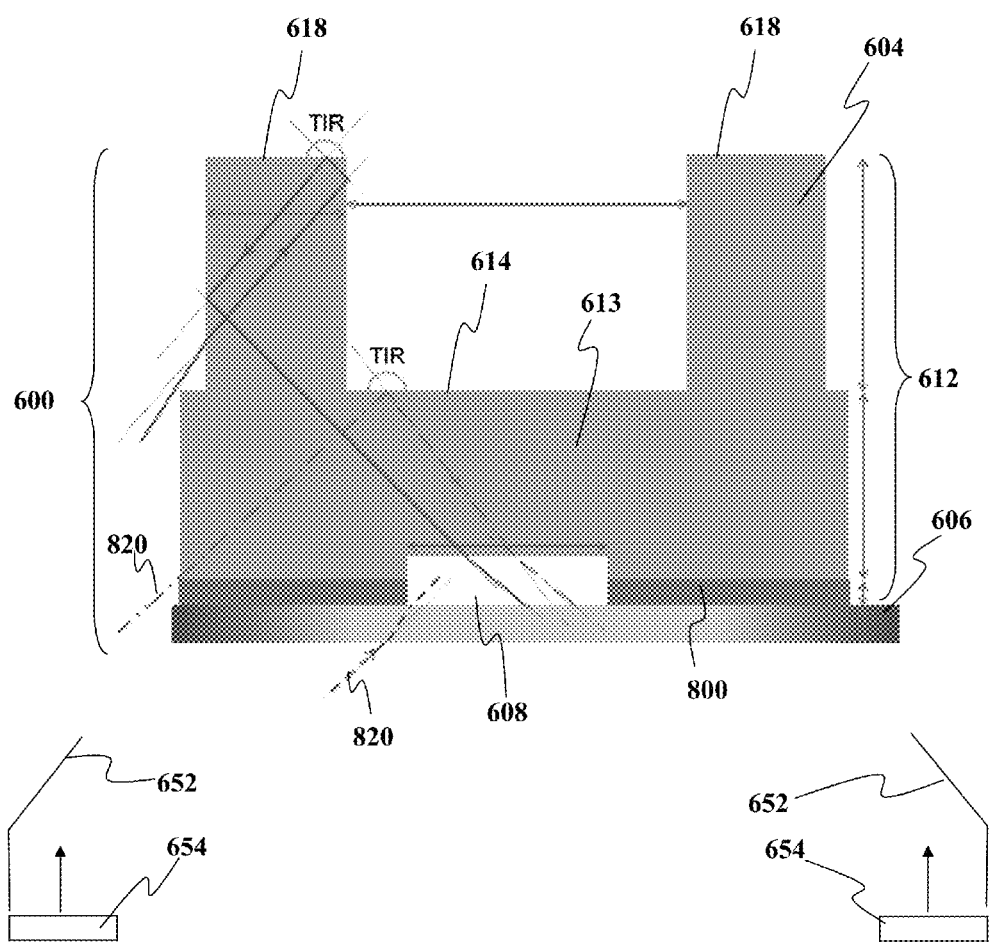

Referring now to FIG. 8, a still further embodiment will now be described. FIG. 8 shows a schematic of a cross-section of a portion of the cuvette 600 and the dark field scatter illumination source such as but not limited to the ringlight 650. For ease of illustration, the support structure 620 is not shown. As seen in FIG. 8, the ringlight 650 provides illumination for the analysis area 608. In the present embodiment, the ringlight components 652 and 654 are shown. The light source 654 may be white light or light sources such as but not limited to LEDs or laser diodes with specific wavelength output or output ranges. Optionally, the ring of light source 654 could be fiber optic cable with many splice to create a ring of light. Optionally, the light source 654 may be an LED which has specific narrow divergence angle controlled by the reflector. It may be desirable to control divergence angle from the ringlight through the selection of light source and/or design of the reflector.

By way of nonlimiting example, laser illumination as the source 654 provides for narrow light pattern with results in lower trans illumination in the present epi-style lighting configuration (where illumination components are all on one side of the sample) but because the source is a coherent source, it also lowers background signal levels. Laser illumination may not have adjacent channel illumination that typically occurs with more diffuse light sources and thus less, laser illumination can result in less trans illumination. Of course, it is desirable that the decrease in trans illumination is less than the decrease in background, where the more significant drop in background results in a more distinguishable signal. Optionally, LED as the illumination source 654 provides for a diffuse light pattern, with increased background and increased trans illumination. Of course, it is desirable that the increase in trans illumination is greater than the increase in background.

Some cuvette embodiments may include cuvettes formed from a plurality of individual layers adhered together, having the cuvette molded from one or more materials, and/or having reflective layers added to the cuvette at different surfaces to enhance multiple TIR.

Because the present embodiment may be operating in combination with fluorescence, desirable that our darkfield illumination is not white light. Some alternative embodiments may use just white light if their system is not using fluorescence detection in combination with darkfield and/or brightfield microscopy.

FIG. 8 shows that in some embodiments, the device may have layers in the cuvette 600 that are optically non-transmissive such as layer 800. This may be useful in embodiments where the light source 654 is diffuse and light is not directed to specific locations. The layer 800 can block light that are not entering the cuvette 600 at desired angles and/or locations. The layer 800 can be configured to be positioned to prevent illumination except through the area below the analysis areas 608. Some may only have specific areas that are blacked out nearest the analysis areas 608. Some embodiments may have blacked out or non-tranmissive material in more than one layer. Some may have blacked out or non-tranmissive material in different orientations, such as but not limited to one being horizontal and one being vertical or non-horizontal.

FIG. 8 shows that total-internal-reflection (TIR) may be present at an upper surface 614 and/or at surface 618 in one or more of the support structures 604. TIR is a tunable feature that can selected based on the material used for the cuvette 600 and the geometry and/or thickness of the controlled thickness area 613 of the cuvette 600. The presence of TIR which allows for oblique angle illumination coming from above the sample is desirable, particularly for darkfield microscopy. In some embodiments, it is desirable to maximize TIR from above the sample. Optionally, some embodiments may only have TIR from surfaces over the analysis areas 608. Optionally, some embodiments may only have TIR from surfaces over the controlled thickness areas 613. Optionally, some embodiments not have TIR from the support structures 604. Optionally, some embodiments not have TIR from surface 618. Optionally, some embodiments may have TIR from other surfaces in the cuvette 600, so long as it is scatter light as oblique angles being directed back to the analysis area 608.

Optionally, some embodiments may put reflective material at surfaces 614 and/or 618. Optionally, only surface 614 has reflective material on the surface. Optionally, surface 618 may be treated to be black so as to be light absorbing. Some embodiments may select the width of the controlled thickness area 612 to be wider than the analysis area 608. For some embodiments using laser illumination, the layer 800 may be removed or be light transmitting as the laser illumination is sufficiently focused so as not to require blackout between analysis areas 608.

By way of example and not limitation, the use of TIR can also enable light 820 from adjacent areas to be directed into the analysis area 608. Under traditional terminology, this is trans illumination. Line 830 shows light coming directly from the ringlight and not by way of TIR, and this is epi illumination. The combination of both types of light components from a light source located below the sample (or only one side of the sample) allows for improved performance as compared to sources that can only provide one of those lighting components. This is particularly useful for darkfield microscopy.

One nonlimiting example of the use of the embodiment shown in FIG. 8 is darkfield illumination to measure scatter properties of cells in the sample. Darkfield microscopy is an age old method that has been used mainly as a contrast enhancing technique. Since only the light scatter or reflected by the sample is imaged, the image background is fully dark. Quantitative darkfield microscopy has not been used to measure scatter properties of cells comparable to the traditional "side scatter" parameter in flow cytometers.

From the hardware perspective, illumination for darkfield microscopy is desired to be oblique, i.e. no rays of light from the illumination light source should be able to enter the objective without contacting the sample first. By way of example and not limitation, illumination should be at a wavelength that does not excite any other fluorophores already present in the sample. Optionally, this illumination allows for the use of high numerical aperture (NA) lenses for imaging. By way of example and not limitation, for traditional lens sizes associated with optical microscopes, the NA may be at least 0.3. Optionally, the NA is at least 0.4. Optionally, the NA is at least 0.5. Optionally, some embodiments may use oil immersion objective lenses to obtain a desired NA, particularly when lens size is limited below a certain level.

Traditional methods for darkfield illumination have used trans-illumination, where the sample is between the imaging lens and darkfield light source. Thus, in this embodiment, the detection and illumination components are not on the same side of the sample. The epi-illumination methods (where the imaging lens/objective and the darkfield light source are on the same side of the sample) require the use of specially manufactured objectives and typically do not allow the use of high NA objectives, thus limiting the capabilities of the whole system.

By contrast, at least some embodiments of darkfield illumination systems described herein have the following attributes. In terms of hardware, the scheme of this embodiment of FIG. 8 is "epi" in that the ringlight used for darkfield illumination is on the same side of the sample as the objective. This can be desirable from the system-perspective, although alternative embodiments with light sources on the other side may be used alone or in combination with the embodiments described herein. In one nonlimiting example, the ringlight is designed such that the LEDs and/or lasers of the light source 654 are all in the same plane and have the same orientation (horizontal plane and directing light upwards). Some embodiments may have light in the sample plane but directing light in a non-parallel manner, such as but not limited to a cone-like manner. Some embodiments may have light in different planes but directing light in the same orientation. Some embodiments may have light in different planes but directing light in a non-parallel manner, such as but not limited to a cone-like manner. The light is reflected by a toroidal mirror 652 to achieve oblique illumination of the sample.

In addition to the ringlight and the toroidal reflector, the optical properties of the cuvette 600 shown in the embodiment of FIG. 8 also significantly affects darkfield illumination. In this embodiment, the cytometry cuvette 600 is designed such that light coming from the ringlight 650 is allowed to fall directly on the sample; but in addition to this, light is also "reflected" on the sample from features of the cuvette so as to emulate "trans" illumination. This reflection can be by way of TIR and/or true reflection.

Note that any trans-illumination scheme allows one to measure forward scattered light from a particle whereas an epi-scheme allows one to measure only the back-scattered light. Forward scattered light is generally two orders of magnitude greater in intensity than the back-scattered light. Trans-scheme thus allows the use of much lower illumination intensities and reduces harmful side effects on the sample.

As seen in the embodiment of FIG. 8, the ringlight 650 and cuvette 600 provide a system that can be tuned such that the intensities of trans and epi illumination are adjusted for improved performance over traditional epi illumination. This tuning can be achieved by virtue of cuvette geometry to control angles and extent of total internal reflection and material properties.

Darkfield

At least some embodiments herein include a dark field illumination source and cuvette. The relevant features of the cuvette 600 relate to designing the cuvette dimensions and optical materials and the geometry of the cuvette. The cuvette increases the extent of darkfield illumination through total internal reflection (TIR) and/or pure reflection. In one embodiment, the system may simultaneously use trans darkfield and epi darkfield.

In some embodiments herein, the cuvette combined with the light source enables trans and epi illumination using only physical system in epi configuration (light source on one side of sample). The basic cuvette is designed to contain the biological sample and present it for visualization. In one embodiment, the coverslip 612 may have a specific design. Materials have different index of refraction. Some embodiments may make cover slip 612 of glass.

One can design the material of the top coverslip 612 to facilitate illumination and image collection. To get light to the cells, the ringlight 650 may be circular, have light sources 654 position in a discrete or continuous pattern, and use a curved reflector 652 to direct light to the sample.

In darkfield microscopy, the sample is illuminated by oblique rays. The light going into the microscopy is the light scattered by the sample. Measuring scatter properties of the cells. If nothing is there, the image is black.

In the present non-limiting example, the reflector 652 and LED 654 of the ringlight 650 are designed to reflect so that a minimum fraction goes directly back into the objective as non-specific background. The system is designed to give TIR surface and reflection from other surfaces back into the target area 608. The cells in the sample in 608 is getting light directly from the ringlight from underneath the cell (this is epi). There is also light coming from the top surfaces (reflected) and this is trans.

With the ringlight 650 in the same position, one now has light coming from two directions from a single ringlight source. This is all oblique. One can control the relative strengths of the two light components by design of the cuvette and material used for the cuvette.

This darkfield illumination is different from conventional darkfield. By way of nonlimiting example, this embodiment may use a reflective layer on the backside of certain surfaces of the coverslip 612 to reflect all of the light. Some embodiments may use a full or selectively reflective background.

In the present embodiment, the light is desirable at an oblique angle which keeps illumination darkfield. Some may angle the light sources 654 at an angle and thus not use the reflector 652. The reflector 652 may improve manufacturability of the light source 654 since all lights are in the same plane, directed in the same direction. Optionally, the angled light sources 654 may also be used in place of or in combination with a reflector.

It should be understood that here even though trans component may be in one example 10 times weaker than epi illumination component, the scatter from the cells in the sample due to trans may be 200 times stronger from the same amount of epi versus scatter from the same amount of trans. And thus, the small amount of trans can significantly enhance the scatter from cells. The light collected from epi illumination also does not include defraction. Defraction is a substantial component of scatter and the use of trans illumination provides for some amount diffraction. Thus, there is reflective, refractive, and defractive components when using trans and epi illumination. With epi alone, there may be only reflective. Traditional methods uses all trans darkfield illumination which takes significant amount of space to configure, due to components being on both sides of the sample. The present embodiment may obtain the space savings of an epi configuration but still have epi and trans illumination components on the sample.

Designing the sample holder and the light source together can enable an epi configuration to increase the amount of trans illumination, particularly uniform trans illumination. Some embodiment may use mirrored surfaces but TIR can be tuned to create the desired trans lighting that is uniform and at oblique angles into the analysis area for darkfield illumination of the sample. In one nonlimiting example, a thicker top 612 allows the TIR to come back into the target area 608. Traditional hardware may have some TIR but the light may not come back into the area 608. Additionally, not just that TIR illumination comes back into the channel but that it comes back uniformly. This embodiment of FIG. 8 has certain surfaces at certain angles, has certain black surface(s), and certain reflective surface(s) so that the light comes back uniformly. Optionally, one could put a fully reflective surface on a top (such as but not limited to a flat top but optionally over select areas of top 612 such as area 613).

By way of nonlimiting example, embodiments here take an imaging based platform and instead of using a high complication, high cost system which may for example have 16 laser, the present embodiment leverages a more integrated detection system to be able to pick-up the differentials of cells and types.

In one nonlimiting example, it is the combination of all these different types of information to achieve the clinical goals. This may include quantitative and/or qualitative linked to quantitative, or images linked to quantitative measurements. Not only different channels of fluorescence where each channel may have one or more specific molecular markers targeted and that is quantitative information, but with microscopy, some embodiments herein have the ability to look at the background that staining forms inside the cell (whether it is in the cytoplasm, is it concentrated on the surface, in the nucleus,) that can link image and/or qualitative information that generated the quantitative measurements. In this manner, the linkage of the original images that created the quantitative results are available for further analysis if it turns out that the quantitative measurements trigger alarms or meet thresholds the suggest further analysis is desired. Embodiments herein can interrogate background staining creates in the cell. One can image if the staining is in the cell, the cytoplasm, etc. . . .

Some embodiments herein may be combining the quantitative scatter properties of the cell, the shape of the cell, and/or the size of the cell. Some embodiments here measure the physical properties, optical properties, and bio/biochemical properties all in the same device at the same time. All can be combined in a programmable processor or other processing system link the various types of information to achieve the clinical goal of the assays.

Many traditional devices do one or the other. They do not do both and there is also no linkage between different types of information. Some embodiments herein, where image information is retrievable that generated the quantitative measurements, can be extended to tissue morphology measurement. It can be applied to pap smear, which is traditional cytology. It can be extended to anything done using traditional microscopy. In urine, the present embodiments can look at and analyze crystals and not just cells. One can look at crystals of inorganic salts and chemicals from urine samples that had created certain quantitative readings on one portion of a graph, such as but not limited what may be seen in FIG. 1A where different regions of data are circled. Image information for certain data regions can be retrieved to further analyze the underlying cell images that created the measurements plotted on the graph or chart.

Some embodiments herein combine the imaging features with the pathology features. For example, tissue prep may occur inside a blade or module, and such prepped material can be imaged in this platform. Then the images or analysis is sent to servers to do image analysis to do diagnosis or digital pathology to enable a pathologist to do analysis.

Esoteric Cytometry and Specialty Cytometry Marker

Many traditional advanced or esoteric cytometric assays require a traditional system to measure a large number of markers on cells, typically simultaneously. The general approach in the field have been tied to high capability instruments such as six or other multiple numbers of lasers and 18 different PMT tubes to measure all of these parameters simultaneously. Part of it has been dictated by traditional methodology of identifying all markers on a cell at the same time, which has driven it. However, in many clinical settings, this simultaneous measurement is not the requirement. In many clinical requirements, one is interested in seeing how many cells are positive for one marker, how many are positive for a combination of two or three markers. Some embodiments herein provide for multiple combinations of staining schemes where one may have a set of, for example, 10 markers, where one can combine them in sets of 3-4 or 5-6 markers where one can combine them such that even if combining two markers in the same color, some embodiments of the present system can de-convolute which signal came from which marker. This allows some embodiments of the present system to reduce the hardware requirements in terms of the number of light sources, the number of channels used for sample analysis. Thus, using subsets or markers in non-simultaneous manner in a pre-determined pairing can be useful to enable esoteric cytometry. Perhaps certain markers are "gating" markers and they can be tested first and if the results are negative, then other follow-on markers may not be need. Some embodiments herein using this non-simultaneous system also reduces the sample volume requirement.

It should be understood that by using imaging, the ability to get an actual count, it may be more accurate than traditional cytometry. Traditional flow cytometry gating does not allow for actual count. Imaging can actually be more accurate. The gating in flow cytometry is subjective and thus this can vary from system to system.

Some embodiments herein may also gate, but the gating is based algorithmically based on various factors including but not limited to patient health. Classification means is trained on a population of patients knowing if they are healthy or diseased. Some embodiments here can flag a patient that is abnormal and flagging it for review. Self learning gating can determine if different gating is desired based on information conveyed regarding the patient health. Thus, the gating for some embodiments herein for the sample is done algorithmically, possibly with a programmable processor, and the gating changes based on patient health.

Imaging: in many cases, one may want to minimize hardware capability and to re-use the sample volume. Thus, the more capability one can extract from the imaging, the better in terms maximizing information from even less sample. Thus, the more information one can get to differentiate different cell types from minimum number of pictures, the more one may minimize the sample volume required.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, different materials may be used to create different reflective surfaces in the cuvette or other surfaces along a light pathway in the optical system. Optionally, the reflective surface is selected so that the reflection is only diffusive. Optionally, the reflective surface is selected so that the reflection is only specular.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes:

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

What is claimed is:

1. A system for analyzing a sample, the system comprising:
    A detector;
    An illumination source;
    A cuvette comprising a base portion, an analysis portion for holding said sample, and a cover portion, said base portion comprising a transparent material, said analysis portion being disposed on a first side of the base portion, and the base portion having a second side opposite to said first side, said cover portion comprising at least one TIR surface configured to reflect light from said illumination source by total internal reflection (TIR) towards said analysis portion, wherein said TIR surface is parallel with the first side of the base portion;
    Wherein both said detector and said illumination source are disposed nearer to said second side of the base portion than to the first side of the base portion, effective that the base portion is disposed between the analysis portion of the cuvette and the illumination source, effective that the base portion is disposed between the analysis portion and the detector, and effective that the sample disposed in said analysis portion is disposed between the illumination source and said TIR surface;
    Wherein the illumination source is configured to direct light towards the base portion of the cuvette, wherein said light passes through said second side of the base portion before passing through said first side of the base portion of the cuvette effective that:
    1) a first portion of the light travels along a path that emerges from the base portion and provides direct epi-illumination light directed to the analysis portion without reflection; and
    2) a second portion of the light travels along a path that emerges from the base portion, continues within the cover portion to said TIR surface of the cover portion configured to reflect light from the illumination source by TIR, effective to provide TIR reflected trans-illumination light directed to the analysis portion;
    wherein the system is configured to simultaneously provide both said TIR reflected trans-illumination light and said direct epi-illumination light to the sample located in the analysis portion of the cuvette.

2. The system of claim 1, wherein the cuvette comprises at least one optically non-transmissive surface.

3. The system of claim 1, wherein the base portion comprises an optically transmissive surface on each of said first side and said second side and is configured to pass light from the illumination source to the sample located in the analysis portion of the cuvette.

4. The system of claim 1, wherein the illumination source comprises a ringlight and an optical pathway from said ringlight to the cuvette.

5. The system of claim 4 wherein the ringlight comprises a light-emitting diode (LED) ringlight.

6. The system of claim 4 wherein the ringlight comprises a laser-based ringlight.

7. The system of claim 1, the base portion further comprising an optically clear surface shaped to engage an optically clear surface of the cover portion of the cuvette.

8. The system of claim 1 wherein the cuvette comprises a channel, and wherein said detector is configured to image a portion of the sample within said channel in the cuvette.

9. The system of claim 1 wherein the cuvette comprises a channel, and wherein the detector is configured to image the entire sample within said channel in the cuvette.

10. The system of claim 1 wherein the analysis portion of the cuvette is configured to hold the sample in a static, non-flowing manner during imaging.

11. The system of claim 1 wherein the analysis portion of the cuvette is configured to hold one portion of the sample in a static, non-flowing manner and another portion in a flowing manner during imaging.

12. The system of claims 1 wherein the cuvette is configured to hold the sample in a flowing manner during imaging.

13. The system of claim 8, wherein the cuvette comprises two or more sample channels for holding the sample or a portion thereof.

14. The system of claim 1 wherein the sample remains separate from a detector in a fluid circuit fully confined in the cuvette, where the cuvette is movable relative to the detector.

15. The system of claim 1, wherein the cover portion of the cuvette has a step-shaped vertical cross-sectional shape.

* * * * *